(12) United States Patent
Sweis

(10) Patent No.: US 10,322,249 B2
(45) Date of Patent: Jun. 18, 2019

(54) MARKING TEMPLATE FOR MEDICAL INJECTIONS, SURGICAL PROCEDURES, OR MEDICAL DIAGNOSTICS AND METHODS OF USING SAME

(71) Applicant: Iliana E. Sweis, Northbrook, IL (US)

(72) Inventor: Iliana E. Sweis, Northbrook, IL (US)

( * ) Notice: Subject to any disclaimer, the term of this patent is extended or adjusted under 35 U.S.C. 154(b) by 325 days.

(21) Appl. No.: 15/162,952

(22) Filed: May 24, 2016

(65) Prior Publication Data

US 2017/0340840 A1 Nov. 30, 2017

(51) Int. Cl.
*A61M 5/42* (2006.01)
*A61B 90/00* (2016.01)
*A61M 5/00* (2006.01)

(52) U.S. Cl.
CPC .............. *A61M 5/427* (2013.01); *A61B 90/39* (2016.02); *A61M 5/007* (2013.01); *A61B 2090/395* (2016.02); *A61B 2090/3937* (2016.02)

(58) Field of Classification Search
USPC ........................................................ 600/431
See application file for complete search history.

(56) References Cited

U.S. PATENT DOCUMENTS

| 7,713,234 | B2 | 5/2010 | Karanzas | |
|---|---|---|---|---|
| 8,075,525 | B2 | 12/2011 | Yang | |
| 8,133,201 | B1 | 3/2012 | Hurtado | |
| 2004/0153031 | A1 | 8/2004 | Van Kaauwen | |
| 2005/0148935 | A1* | 7/2005 | Dimitrova | A61M 5/427 |
| | | | | 604/116 |
| 2010/0015590 | A1 | 1/2010 | Kiss | |
| 2013/0231583 | A1* | 9/2013 | Rekkerth | A61B 5/445 |
| | | | | 600/556 |
| 2014/0039658 | A1 | 2/2014 | Bangera et al. | |
| 2014/0257183 | A1* | 9/2014 | Mica | A61M 5/427 |
| | | | | 604/116 |

FOREIGN PATENT DOCUMENTS

WO 2015/085019 6/2015

* cited by examiner

*Primary Examiner* — Nicole F Lavert
(74) *Attorney, Agent, or Firm* — Morgan, Lewis & Bockius LLP; Christopher J. Betti

(57) ABSTRACT

The present disclosure provides a template for marking injection sites on a biological surface prior to performance of a medical procedure, wherein the template comprises a flexible sheet having marked positions or demarcated areas for each injection site, and wherein each marked position or demarcated area is associated with a unique identifier. Also provided are methods of using such disclosed templates in a medical procedure where an agent or material is injected into a patient.

17 Claims, 10 Drawing Sheets

FIG. 3

| ·1A | ·2B | ·3C | ·4D | ·5E |
| ·6F | ·7G | ·8H | ·9I | ·10J |
| ·11K | ·12L | ·13M | ·14N | ·15O |
| ·16P | ·17Q | ·18R | ·19S | ·20T |

FIG. 6A

| · 1 | · 2 | · 3 | · 4 | · 5 |
|---|---|---|---|---|
| · 6 | · 7 | · 8 | · 9 | ·10 |
| ·11 | ·12 | ·13 | ·14 | ·15 |
| ·16 | ·17 | ·18 | ·19 | ·20 |

FIG. 6B

| 5 | 4 | 3 | 2 | 1 |
|---|---|---|---|---|
| 10 | 9 | 8 | 7 | 6 |
| 15 | 14 | 13 | 12 | 11 |
| 20 | 19 | 18 | 17 | 16 |

MARKING TEMPLATE FOR MEDICAL INJECTIONS, SURGICAL PROCEDURES, OR MEDICAL DIAGNOSTICS AND METHODS OF USING SAME

FIELD

The present disclosure relates generally to marking templates for medical injections and methods of using such templates in medical, surgical or diagnostic procedures involving the injection of therapeutically active agents including, for example, materials such as fillers and fat into a patient.

BACKGROUND

Certain medical procedures involve the injection of a pharmaceutically active agent at a plurality of positions on a patient's skin. These procedures often employ a template to mark the injection sites on the patient's skin with a removable tattoo. However, such templates do not distinguish one injection site from another. As a result, some injection sites may be over- or under-dosed as a result of human error. Therefore, a need exists for marking a patient's skin in a unique manner such that a physician can readily remember and identify sites that have been or have not been injected with a pharmaceutically active agent. Such a template would reduce human error and reduce and/or prevent over- or under-dosing at an injection site.

SUMMARY

The present disclosure relates to a template for marking injection sites on a biological surface prior to performance of a medical procedure, wherein the template comprises a flexible sheet having unique identifiers that identify positions or demarcated areas for the injection of an agent into a patient. In some embodiments, the unique identifiers are associated with (e.g., positioned next to or near) a marked position for the injection site. In other embodiments, the template comprises a grid having several demarcated areas that are each associated with (e.g., positioned next to or near) a unique identifier.

In some embodiments, the unique identifier is visible.

In some embodiments, the unique identifier is a shape of a number, letter, or any combination thereof on a side of the flexible sheet that contacts the biological surface.

In some embodiments, the unique identifier is pigmented.

In some embodiments, the unique identifier is a combination of a number and a letter.

In some embodiments, the unique identifier is a pigmented combination of a number and a letter.

In some embodiments, the marked positions are equidistant from one another.

In some embodiments, each of the marked positions are 1 cm apart.

In some embodiments, the biological surface is the skin.

The present disclosure also provides methods of marking a biological surface prior to performance of a medical procedure on a subject, the method comprising: applying a template for marking injection sites to the biological surface, wherein the template comprises a flexible sheet having marked positions for each injection site, and wherein each marked position is associated with a unique identifier; and transferring the unique identifiers from the template to the biological surface.

In some embodiments, the unique identifier is visible.

In some embodiments, the unique identifier is a shape of a number, letter, or any combination thereof on a side of the flexible sheet that contacts the biological surface.

In some embodiments, the unique identifier is pigmented.

In some embodiments, the unique identifier is a combination of a number and a letter.

In some embodiments, the unique identifier is a pigmented combination of a number and a letter.

In some embodiments, the marked positions are equidistant from one another.

In some embodiments, each of the marked positions are about 0.5 cm apart, about 1 cm apart, about 2 cm apart, about 3 cm apart, about 4 cm apart, or about 5 cm apart.

In some embodiments, the biological surface is the skin.

In some embodiments, the medical procedure is an injection of fat (e.g., injections to the buttocks), an injection of a soft tissue filler(s), an injection of a fat dissolving agent(s), an injection of a dye(s), an injection of a diagnostic substance(s), an injection of a stem cell(s), an injection of platelet-rich plasma, or an injection of a therapeutic medication(s).

BRIEF DESCRIPTION OF THE FIGURES

FIG. 3 depicts a template for marking injection sites on a biological surface that comprises unique identifiers (shown as a series of numbers and letters) to mark each injection site (represented by a circle). The template may be transferred to a biological surface on a patient by using the template as a stencil that may be colored to mark the unique identifiers and injection sites.

FIG. 6A depicts a template for marking injection sites on a biological surface that comprises unique identifiers (shown as a series of numbers) in a grid to mark each injection site (represented by a circle). The template may be transferred to a biological surface on a patient by using the template as a stencil that may be colored to mark the unique identifiers, the grid, and injection sites.

FIG. 6B depicts a template for marking injection sites on a biological surface that comprises unique identifiers (shown as a series of numbers) in a grid to mark each injection site (represented by a circle). The template may be transferred to a biological surface on a patient by using the template as a tattoo to transfer the unique identifiers, the grid to the biological surface.

DETAILED DESCRIPTION

The present disclosure provides a template for marking injection sites on a biological surface prior to performance of a medical procedure, wherein the template comprises a durable or a flexible sheet having unique identifiers (e.g., an identifier that is different from other identifiers on the template including, for example, all other identifiers on the template) that are each respectively associated with (e.g., positioned next to or near) a position or demarcated area on the template that represents the site for the injection of an agent or material into a patient. The unique identifier may be visible and may be in a shape of a number, letter, or any combination thereof. The marked position may comprise a spot (e.g., a circle or a dot) within or next to the unique identifier to denote an injection site. Such marking templates as disclosed herein are advantageous in that they overcome the problems associated with known templates and permit the marking a patient's skin in a unique manner such that a physician can readily remember and identify sites that have been or have not been injected with an agent (e.g., a pharmaceutically active agent) or material in order to reduce and/or prevent over- or under-dosing at an injection site.

As used herein, a "unique identifier" is a shape, number (see, FIG. 1), letter (see, FIG. 2), symbol, or any combination thereof (see, e.g., FIG. 3) that marks sites (or can be used to mark sites) or demarcates areas (or can be used to demarcate sites) on a biological surface that may or may not be used for the injection of a pharmaceutically active agent. The unique identifiers may be equally spaced from one another or may be spaced apart from one another by varying distances. Further still, the unique identifiers may be of the same or of various sizes as compared to one another. Where the unique identifiers are letters and or numbers such identifiers may be continuous (e.g., 1, 2, 3, 4, 5 . . . ; a, b, c, d, e . . . ) or non-continuous (1, 3, 4, 6 . . . ; a, c, d, f . . . ). The unique identifiers may be similarly or differently colored. In further embodiments, the unique identifier in a row or column may be similarly or differently colored.

Figure 6A:
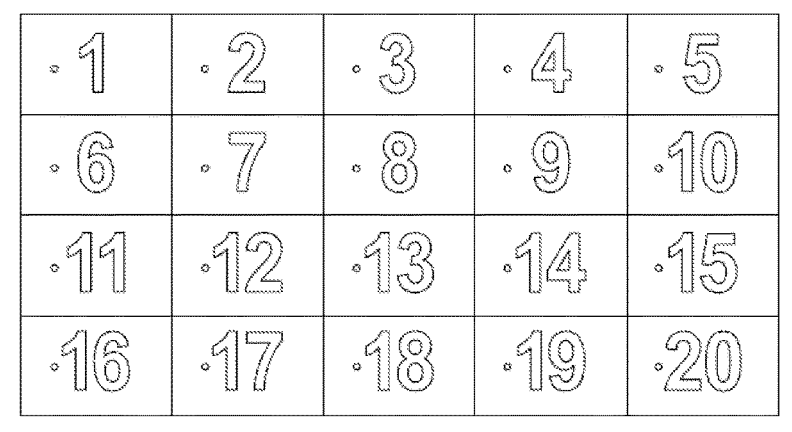
Figure 6B:
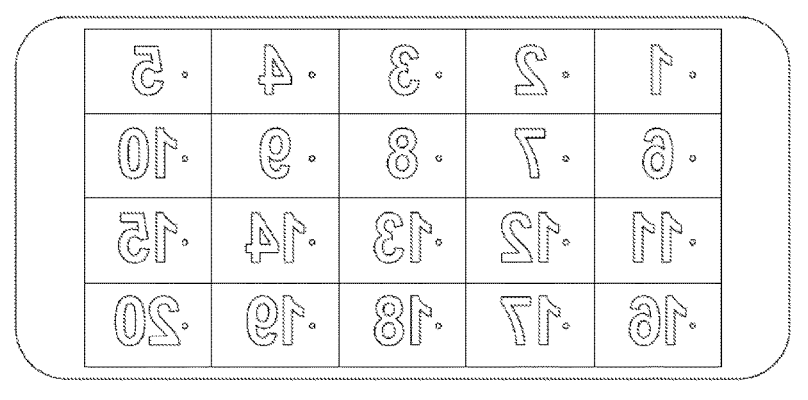
Figure 6C:
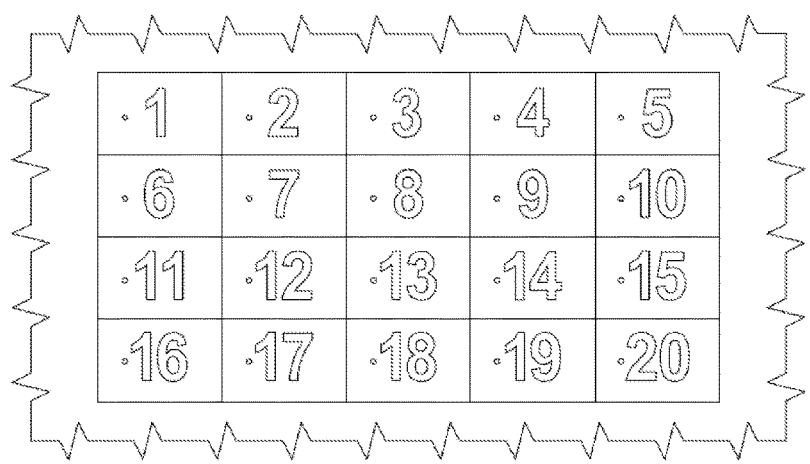
FIG. 6C depicts the surface of a biological surface after the template in FIG. 6B has been transferred to the biological surface.

An injection site may be denoted by a marked position next to or near the unique identifier. Such a marked position may comprise a spot (e.g., a geometric shape such as a circle or a dot) within or next to the unique identifier to denote an injection site. In an embodiment, the unique identifier is the marked position. In some embodiments, the injection site may not be marked by a spot but may rather be demarcated by a grid. In these embodiments, the grid may form a series of boxes (or another geometric shape) with each box demarcating an injection site (see, e.g., FIG. 6A-6C). The injection site can be located anywhere within a box that corresponds to a unique identifier.

Figure 4A:
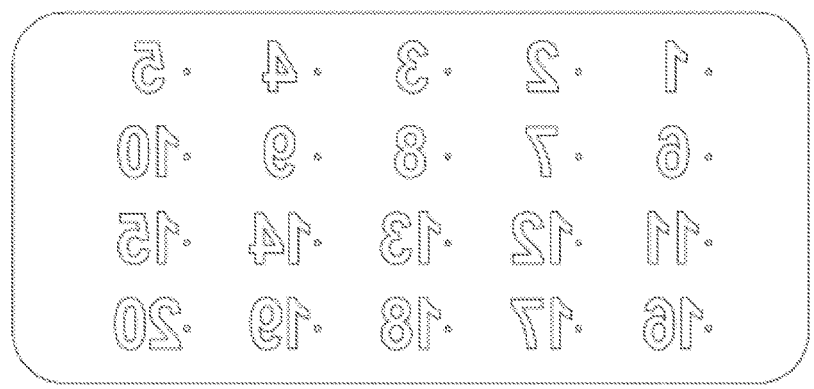
FIG. 4A depicts a template for marking injection sites on a biological surface that comprises unique identifiers (shown as a series of numbers) to mark each injection site (represented by a circle). The template may be transferred to a biological surface on a patient by using the template as a tattoo to transfer the unique identifiers to the biological surface.
Figure 4B:
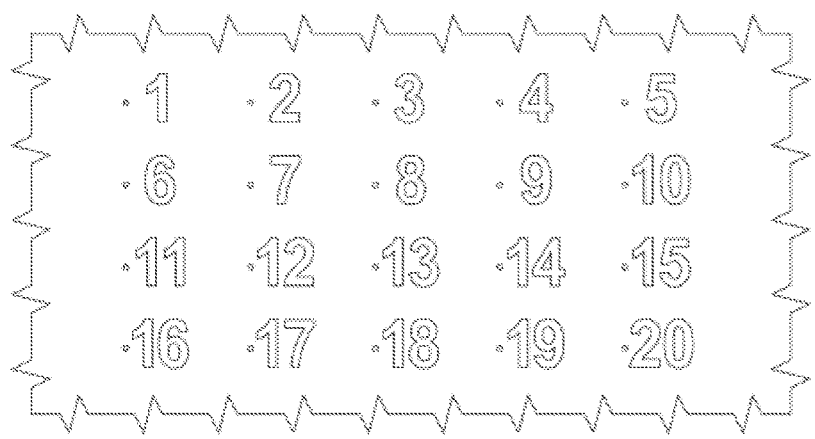
FIG. 4B depicts the surface of a biological surface after the template in FIG. 4A has been transferred to the biological surface.
Figure 5A:
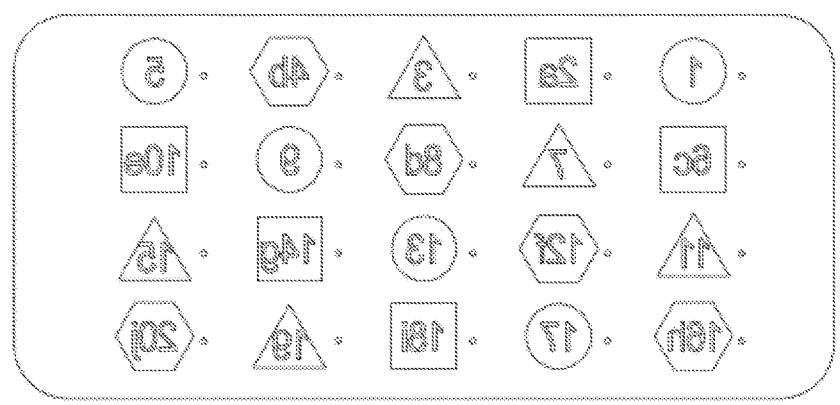
FIG. 5A depicts a template for marking injection sites on a biological surface that comprises unique identifiers (shown as a series of numbers and/or letters) to mark each injection site (represented by a circle). The template may be transferred to a biological surface on a patient by using the template as a tattoo to transfer the unique identifiers to the biological surface.
Figure 5B:
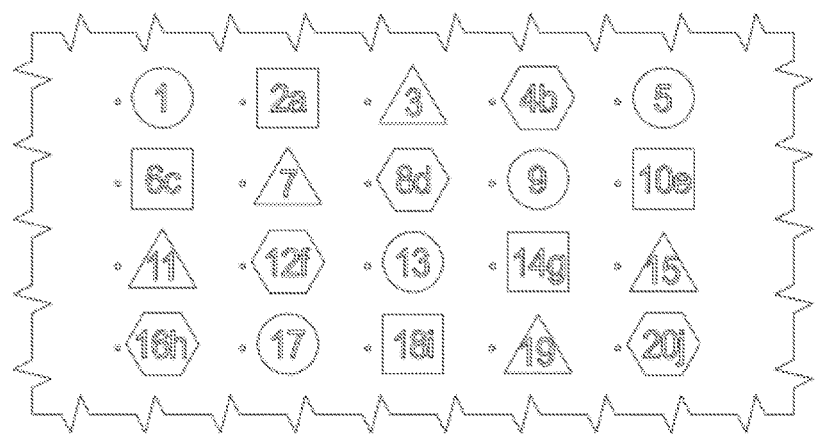
FIG. 5B depicts the surface of a biological surface after the template in FIG. 5A has been transferred to the biological surface.

The marked positions and unique identifiers may be formed by pre-printed non-toxic ink patterns on a surface of the template (i.e., the surface that contacts a biological surface) (see, e.g., FIGS. 4A-4B; and 5A-5B). Such marked positions and unique identifiers may be transferred to a biological surface from the template by applying the template to the biological surface with light pressure and then removing said template leaving the desired ink pattern depicting the template on the biological surface. Alternatively, when placed against the biological surface, water or saline may be applied to the back of the template to transfer the marked positions and/or unique identifiers to the biological surface. After a medical procedure, the marked positions and/or unique identifiers may be washed off the biological surface with an alcohol or some other removing agent.

Figure 1:
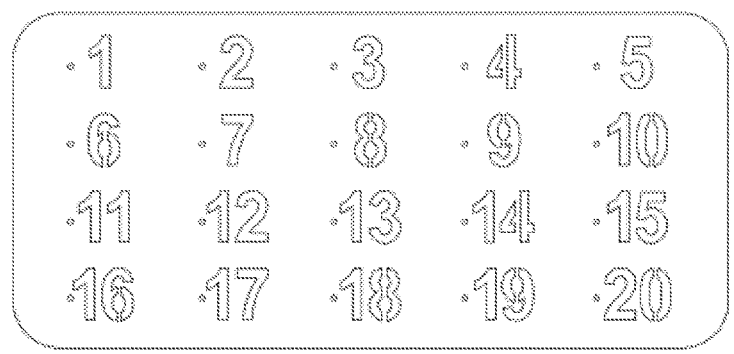
FIG. 1 depicts a template for marking injection sites on a biological surface that comprises unique identifiers (shown as a series of numbers) to mark each injection site (represented by a circle). The template may be transferred to a biological surface on a patient by using the template as a stencil that may be colored to mark the unique identifiers and injection sites.
Figure 2:
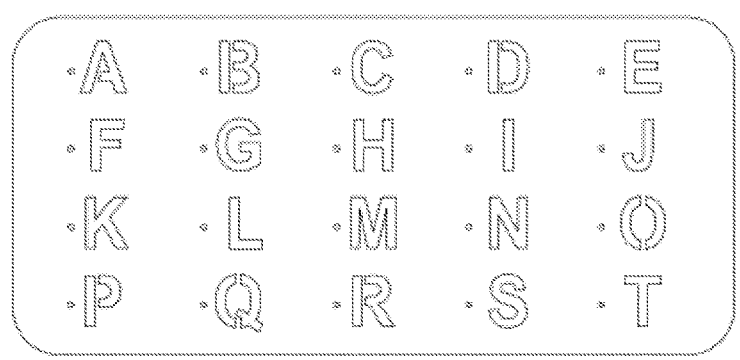
FIG. 2 depicts a template for marking injection sites on a biological surface that comprises unique identifiers (shown as a series of letters) to mark each injection site (represented by a circle). The template may be transferred to a biological surface on a patient by using the template as a stencil that may be colored to mark the unique identifiers and injection sites.

Additionally or alternatively, the marked positions and unique identifiers may be formed by a template that provides a stencil for the marked positions and unique identifiers (see, FIGS. 1-3). Such marked positions and unique identifiers may be transferred to a biological surface from the template by using a writing or coloring device such a marker to color in the void in the stencil that forms the marked position and unique identifier.

The template is preferably comprised of a material that is pliable at room temperature. As such, it preferably may be stretched, bent, flexed, rolled, twisted, or similarly physically manipulated without being easily damaged and after such activities will generally maintain its shape in the configuration into which it has been fashioned. Preferably, the template material will maintain such properties even after repeated manipulation. Additionally, the material is preferably non-allergenic because of its use against the surface of the skin.

The template may a single-use (disposable) template or a reusable template. In embodiments where the template is a reusable template it may be cleaned, disinfected, or sterilized between uses by art recognized methods such as, but not limited to, the use of detergents, alcohol, or autoclaving. Thus in one embodiment the material preferably withstands repeated cleansing, disinfection, sterilization, or any combination thereof without significant deterioration. Still further, the material's physical properties are such that it is sufficiently firm, strong, rigid, etc., to allow the template to function. The material is preferably stretchable or deformable in an elastomeric manner, but alternatively it may be stretchable or deformable in a different manner such as by being viscoelastic or plastic. It is preferable that the material, when at room temperature, will undergo elastomeric deformation when subjected to the forces of manual manipulation. Examples of suitable elastomeric materials include silicone, polytetrafluoroethylene (PTFE), rubber, polyurethane, and other polymers with or without reinforcing materials such as dacron mesh. In view of the foregoing properties, the material allows for the shape of the template, or at least a portion thereof, to be deformed or altered to adjust the shape of the guide portion of the template to assume the desired injection pattern to be marked on the biological surface. The template may be any geometric shape such as a square, triangle, oval, circle, etc. In other embodiments, the template may be an organic shape that conforms to the shape of a biological surface.

The flexible sheet may be die cut or molded with unique identifiers at marked positions (i.e., the unique identifiers are provided by openings in the template). In this manner, the unique identifiers provide a stencil through which the biological surface can be marked with a non-toxic marker pen or other marking implement. By use of the markings on the skin, the template can be removed after placing the marks on the skin. Additionally, in an embodiment, the template further comprises a spot (e.g., a circle or a dot) within or next to the unique identifier to mark an injection site (i.e., the site for insertion of a needle into a biological surface).

In an embodiment, the flexible sheet may comprise a medical grade adhesive on the side of the sheet that contacts the biological surface. In this manner the flexible sheet may remain adhered to the biological surface during transfer of the marking template to the biological surface.

The template may optionally include a strap or belt by which the template can be held in place on a subject's body while adhesive is being applied and without requiring the use of the user's hand to hold the template in place. The template may optionally be coated with a minimally adhering medical grade adhesive on one face by which the template may be held in place on a subject's body while adhesive is being applied and/or marks are made on the skin without requiring the use of the user's hand or a belt to hold the template in place.

The biological surface may be the surface of a tissue or the surface of an organ. Exemplary organs include the skin, the liver, the lungs, the kidneys, the brain, etc. In other embodiments, the biological surface may be a skeletal muscle or a joint.

Methods are also provided to mark a biological surface prior to performance of a medical procedure on a subject, the method comprising: applying a template for marking injection sites to the biological surface, wherein the template comprises a flexible sheet having marked positions for each injection site, and wherein each marked position is associated with a unique identifier; and transferring the unique identifiers from the template to the biological surface.

One or more injections may be made at each marked position on the template that has a corresponding unique identifier. In another embodiment, one or more injections may be made at each marked position on the template that has a corresponding unique identifier.

While the present disclosure has been described and illustrated herein by references to various specific materials, procedures and examples, it is understood that the disclosure is not restricted to the particular combinations of material and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A template adapted for marking injection sites on a biological surface prior to performance of a medical procedure, wherein the template comprises a flexible sheet, wherein the flexible sheet has a surface with an ink pattern for a grid of marked positions or demarcated areas for each injection site, and wherein each marked position or demarcated area is associated with a unique identifier.

2. The template of claim 1, wherein the unique identifier is visible.

3. The template of claim 1, wherein the unique identifier is a shape of a number, letter, or any combination thereof on a side of the flexible sheet that contacts the biological surface.

4. The template of claim 3, wherein the unique identifier is a combination of a number and a letter.

5. The template of claim 3, wherein the unique identifier is a pigmented combination of a number and a letter.

6. The template of claim 1, wherein the marked positions are equidistant from one another.

7. The template of claim 1, wherein each of the marked positions are about 0.5 cm apart, about 1 cm apart, about 2 cm apart, about 3 cm apart, about 4 cm apart, or about 5 cm apart.

8. The template of claim 7, wherein the biological surface is the skin.

9. A method of marking a biological surface prior to performance of a medical procedure on a subject, the method comprising:
   a. applying a template for marking injection sites to the biological surface, wherein the template comprises a flexible sheet, wherein the flexible sheet has a surface with an ink pattern for a grid of marked positions or demarcated areas for each injection site, and wherein each marked position or demarcated area is associated with a unique identifier; and
   b. transferring the unique identifiers from the template to the biological surface.

10. The method of claim 9, wherein the unique identifier is visible.

11. The method of claim 9, wherein the unique identifier is a shape of a number, letter, or any combination thereof on a side of the flexible sheet that contacts the biological surface.

12. The method of claim 11, wherein the unique identifier is a combination of a number and a letter.

13. The method of claim 11, wherein the unique identifier is a pigmented combination of a number and a letter.

14. The method of claim 9, wherein the marked positions are equidistant from one another.

15. The method of claim 14, wherein each of the marked positions are about 0.5 cm apart, about 1 cm apart, about 2 cm apart, about 3 cm apart, about 4 cm apart, or about 5 cm apart.

16. The method of claim 9, wherein the biological surface is the skin.

17. The method of claim 9, wherein the medical procedure is an injection of fat, an injection of a soft tissue filler(s), an injection of a fat dissolving agent(s), an injection of a dye(s), an injection of a diagnostic substance(s), or an injection of a therapeutic medication(s).

* * * * *